(12) United States Patent
St Amant, III et al.

(10) Patent No.: US 9,588,024 B1
(45) Date of Patent: Mar. 7, 2017

(54) STACKED MODULAR CONDITIONING SYSTEM AND METHOD

(71) Applicant: A+ Manufacturing, LLC, Gonzales, LA (US)

(72) Inventors: Valmond Joseph St Amant, III, St Amant, LA (US); Steven Douglas Calverley, Denham Springs, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 156 days.

(21) Appl. No.: 14/198,393

(22) Filed: Mar. 5, 2014

Related U.S. Application Data

(60) Provisional application No. 61/772,880, filed on Mar. 5, 2013.

(51) Int. Cl.
| | |
|---|---|
| G01N 1/00 | (2006.01) |
| G01N 1/22 | (2006.01) |
| G01N 33/00 | (2006.01) |

(52) U.S. Cl.
CPC ....... *G01N 1/2247* (2013.01); *G01N 33/0011* (2013.01)

(58) Field of Classification Search
CPC ......... G01N 1/2247; G01N 2001/2285; G01N 1/02; G01N 35/1065; G01N 35/1095; G01N 35/1097; G01N 2035/0453; G01N 35/1074; E21B 49/084; E21B 49/08
USPC ........................................................ 73/863
See application file for complete search history.

(56) References Cited

U.S. PATENT DOCUMENTS

| | | | | |
|---|---|---|---|---|
| 5,841,036 A | * | 11/1998 | Mayeaux | G01N 1/2035 73/863 |
| 6,122,825 A | * | 9/2000 | Mayeaux | G01N 1/2035 29/890.12 |
| 7,370,674 B2 | * | 5/2008 | Doyle | F15B 13/0817 137/884 |
| 7,472,615 B2 | * | 1/2009 | Mayeaux | G01N 1/2035 374/208 |
| 7,726,331 B1 | * | 6/2010 | Giese | F04D 13/12 137/269 |
| 7,752,928 B1 | * | 7/2010 | Mayeaux | B01L 3/502715 73/863 |
| 7,937,223 B2 | * | 5/2011 | Ciglenec | E21B 49/08 166/100 |

(Continued)

*Primary Examiner* — Freddie Kirkland, III
(74) *Attorney, Agent, or Firm* — Joseph T Regard Ltd plc

(57) ABSTRACT

A system for sampling and/or conditioning a process gas such as natural gas or the like utilizing two or more modular components, each having unique conditioning or monitoring features or the like, which components are formed to be slidingly received in a receiver so as to be stacked one upon the other for sealed engagement, forming a serial flow-through passage to provide conditioning, monitoring, or other features as the gas flows therethrough. An embodiment of the present invention is designed to receive multiple conditioning components, each of which may have diverse functionality such as, for example, one or more stages of pressure reduction, monitoring, particulate and/or liquid droplet filtering, etc. The invention is designed for easy configuration customization so as to provide a readily customizable solution for each application, with an embodiment which may be incorporated into a probe or the like or at its tip, and thereby operate at the prevailing pressure and temperature of the process gas.

53 Claims, 15 Drawing Sheets

(56) References Cited

U.S. PATENT DOCUMENTS

| | | | |
|---|---|---|---|
| 8,322,232 B1* | 12/2012 | Mayeaux | B01L 3/502715 |
| | | | 73/863.85 |
| 8,616,228 B1* | 12/2013 | Mayeaux | F17D 1/00 |
| | | | 137/12 |
| 8,838,390 B1* | 9/2014 | Selman | E21B 44/00 |
| | | | 166/264 |
| 9,200,986 B1* | 12/2015 | Mayeaux | G01N 1/10 |

* cited by examiner

FIG 3B
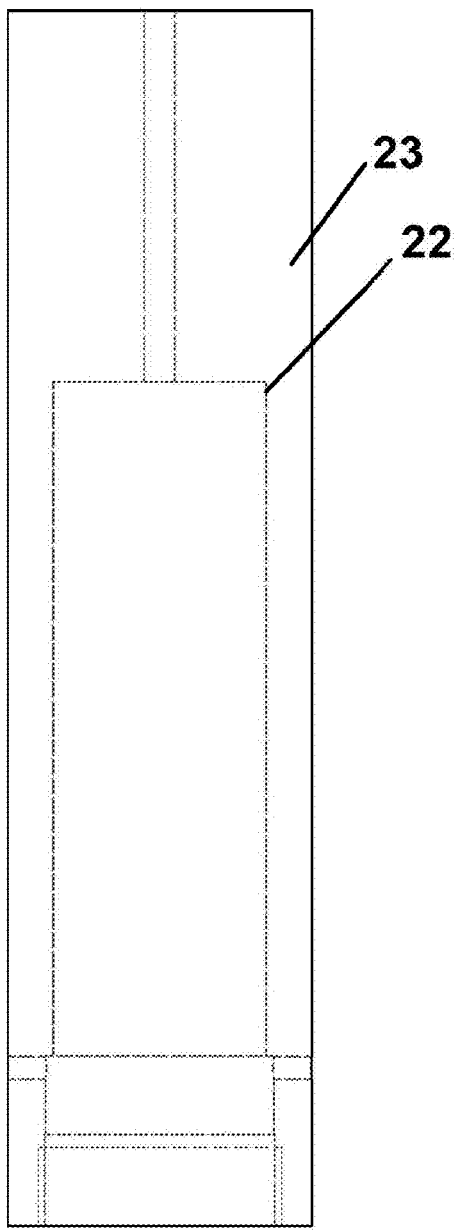
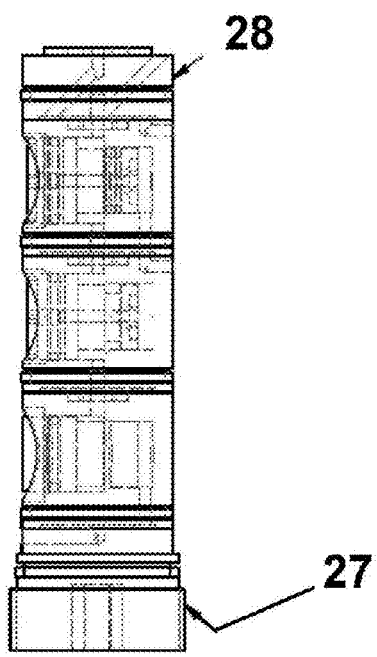
FIG 3A

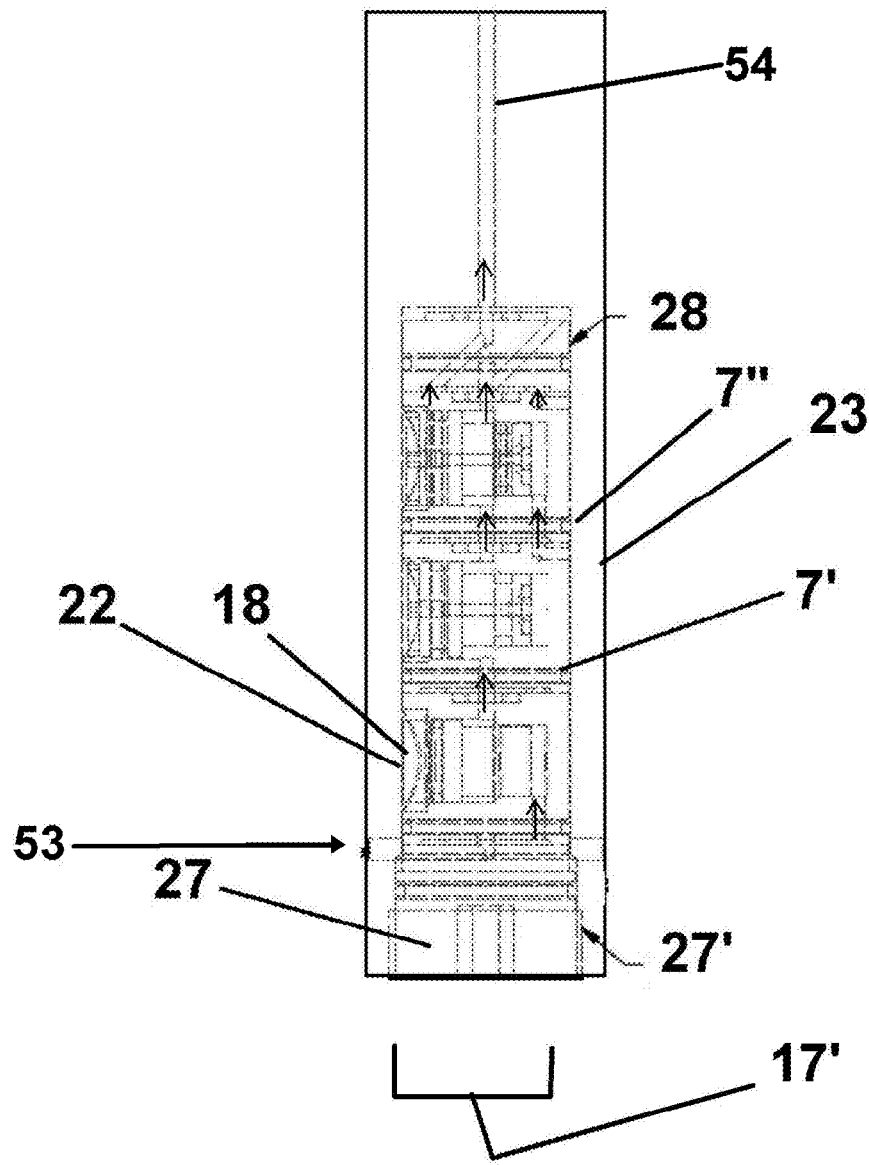

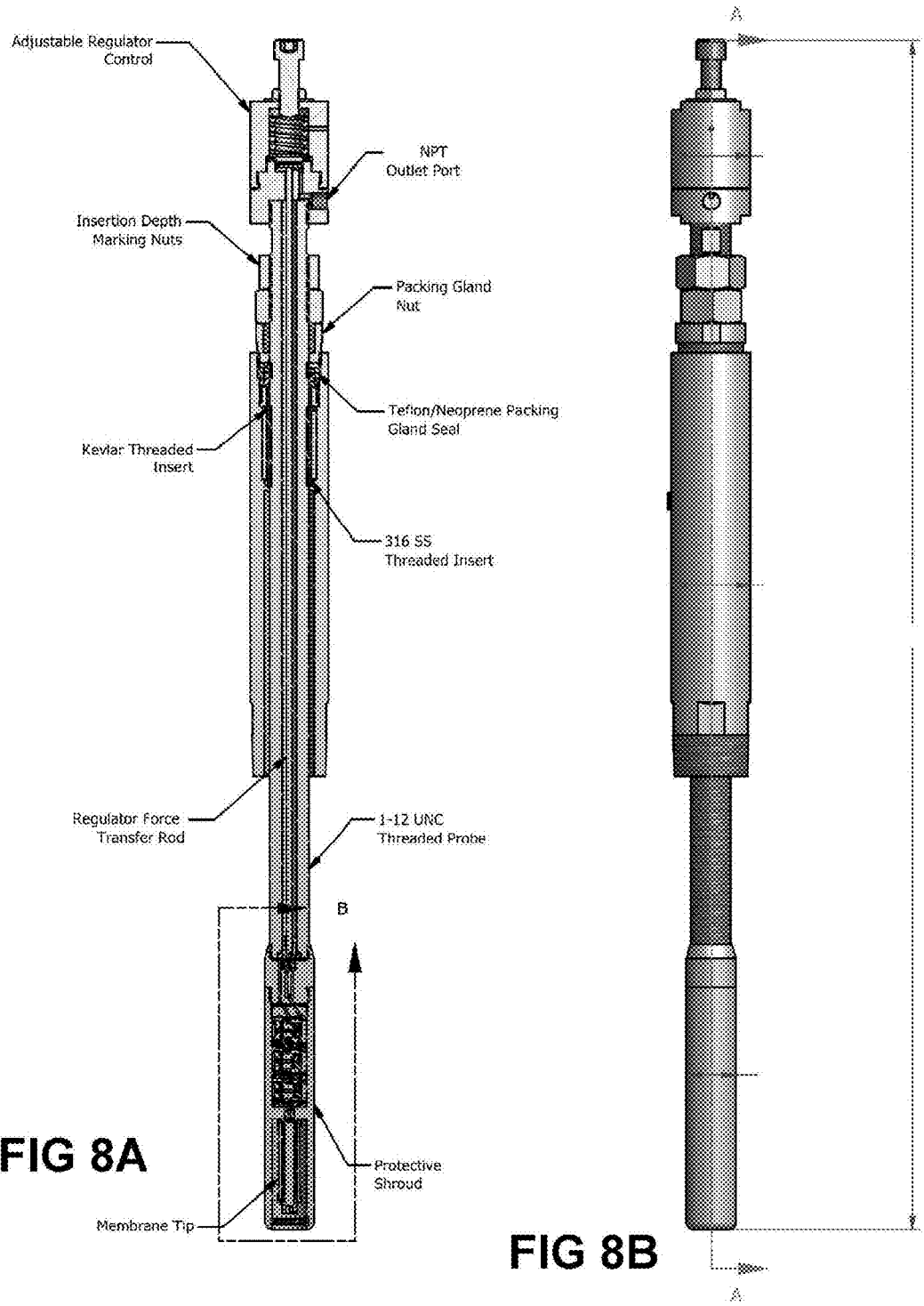

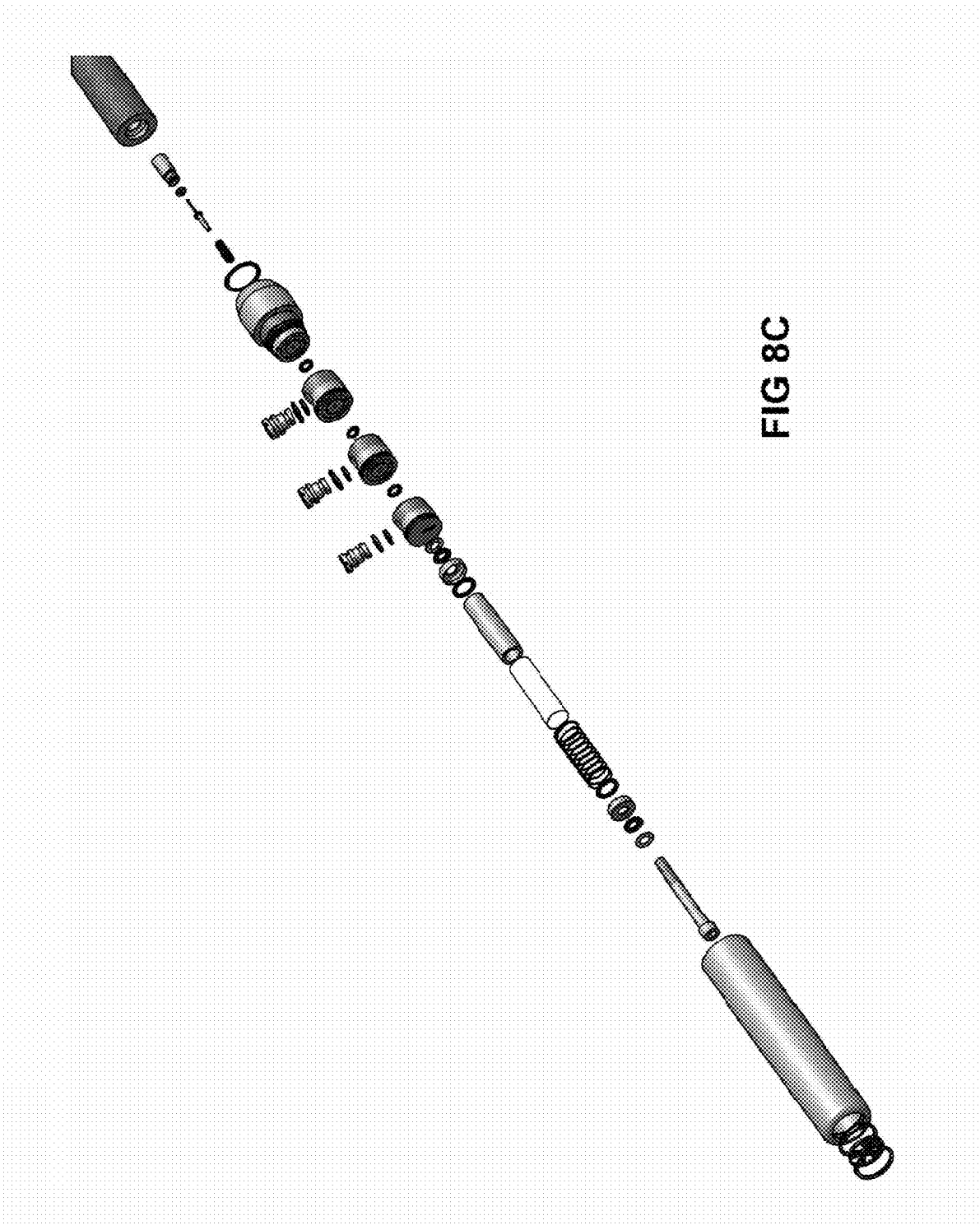

STACKED MODULAR CONDITIONING SYSTEM AND METHOD

BENEFIT CLAIM

The present application claims the benefit of U.S. Provisional Patent Application Ser. No. 61/772,880 filed Mar. 5, 2013 entitled "Stacked Modular Conditioning System and Method", listing as inventors Valmond Joseph St Amant, III and Steven Douglas Calverley.

FIELD OF THE INVENTION

A system for sampling and/or conditioning a process gas such as natural gas or the like utilizing two or more modular components, each having unique conditioning or monitoring features or the like, which components are formed to be slidingly received in a receiver so as to be stacked one upon the other for sealed engagement, forming a serial flow-through passage to provide conditioning, monitoring, or other features as the gas flows therethrough.

BACKGROUND OF THE INVENTION

It is common practice to extract fluid samples from pressurized pipelines or the like for analysis in the field or for off-site, laboratory analysis. This is especially true in the natural gas industry, where the monetary value of the gas is dependent on its compositional analysis. Likewise, the chemical and oil refining industries also have needs for extracting fluid samples from pressurized fluid sources.

Sampling and/or monitoring of the material may take various forms. Probes may be used to extract physical samples from the process gas, which may contain entrained liquid. In addition, real-time or time delayed monitoring via sensors or the like (for example, temperature, flow, liquid phase content, pH, etc) provides information on the process gas and its attributes. Corrosion coupons or other exposure indicators are likewise used to provide valuable data.

When collecting material samples for external use, as well as other operations, it may be necessary or desirable to separate liquids from the sample, or subject the material to other conditioning during the its retrieval such as, for example, pressure reduction, which may be desirable, especially in a sampling scenario involving a high pressure source.

For analytical applications including archiving, testing or the like, it may be important to avoid JT cooling to prevent condensation of vapor phase constituents. In such a case, stepped or otherwise controlled pressure reduction may be desirable to avoid adiabatic pressure drop, which may occur where to great a pressure drop is made in a single stage of pressure reduction. This should be avoided as too great a pressure drop in a single stage could result in JT cooling of the gas below its hydrocarbon dew point, resulting in sample gas composition distortion and potentially inaccurate data on the process gas stream.

Multi-stage, prior art pressure regulators can be bulky and typically are limited to two stages, and in the past, little or no consideration was given to minimizing the J-T cooling effect in third party systems.

Past modular sample conditioning systems employing two or more stages have been typically bulky and located external the fluid source, may be exposed to the elements and ambient temperature (unless insulated and/or heated or cooled to the temperature of the flow stream), and may require specialized on-site setup and calibration.

Current modular sample conditioning systems are comprised of individual sample conditioning components mounted a plate or base module near the analyzer. Examples of such systems include Parker's Intraflow system, Swagelok, and Circor Tech. These current modular sample conditioning systems are housed near the analyzer, typically in heated analyzer shelters.

GENERAL SUMMARY OF THE INVENTION

Unlike the prior art, the present invention contemplates a modular sample conditioning system which is compact, robust, easily assembled, diverse in conditioning capabilities, and able to be utilized as a probe tip or otherwise in conjunction with a sample probe or the like, or other use, and thus operate at the prevailing pressure and temperature of the process gas stream.

The present system is designed to provide a modular sampling system assembly having diverse functionality, and which can be easily customized for each application, and easily reconfigured as the need arises by a user, without the need for extensive training.

For example, the system of the present invention may be used for sampling and/or conditioning natural gas in preparation for analysis, using multiple stacked internal analytical sample conditioning components that may be utilized inside a probe that is inside a pressurized vessel such as a pipeline or other pressurized vessel or the like. A benefit of such an installation is that the components would be at the prevailing temperature and pressure of the interior of the vessel, and would not require additional shelter or enclosure, providing a reduced footprint.

The preferred embodiment of the present invention comprises a conditioning assembly comprising a receiver formed to slidingly receive conditioning components which are stacked upon one another for serial flow therethrough. The components utilized in the present device may comprise, for example, component bodies formed to receive sample conditioning sub-components such as membrane separators (e.g., phase separation membrane) regulators and regulator components, isokinetic sampling components, coalescing filters, particulate filters (screens, sintered metal, sintered plastics, thermoplastics, borosilicate glass, etc.), inertial separators, valves (i.e., throttling, needle, metering, ball, switching, etc) and others. A single sub-component could be formed to have a single function, or multiple functions, as desired.

The term "conditioning component" is not intended to be limiting as other components may likewise be used in the present invention, including sensors and monitoring components such as corrosion coupons, wireless monitoring devices such as temperature sensors (for example, thermistor sensors, thermometers, etc) wireless monitoring devices, flow meters, pressure sensors, moisture sensors, gas sensors (e.g. H2S and others) liquid detectors, etc. One functional commonality of the above components is that the fluid passing therethrough (which may comprise gas or a gas with liquid suspension, or even liquid) interacts with each said component in some capacity, be it to, for example, condition (in the case of a phase separation membrane, pressure regulator, etc) or provide data in a monitoring context (in the case of temperature sensors, flow meters, pressure sensors, etc), so the term "interacted fluid" may be used to describe fluid which has passed through any of the above components.

The present invention would be particularly suitable for providing a series of pressure regulators in stepped reduction stages to limit or prevent JT cooling, as shown in FIGS. 7-8F in the present application. An example of the use of stepped pressure reduction using pressure regulators in series may be found in Mayeaux now U.S. Pat. No. 8,616,228, the content of which are incorporated herein by reference thereto.

It is stressed that the above component list is intended to be illustrative only, and not limiting, as there are many other conditioning/monitoring components which may likewise be used with the present system. This is because the present invention is not on the conditioning/monitoring devices/techniques per se. Rather, the present invention provides a modularized system to readily assemble/customize a conditioning/monitoring solution to meet a users demands, as an easily customizable solution is not believed readily available, and there is a long felt, but unresolved need for such a solution, especially when one considers that the every fluid (in the preferred embodiment in this case, natural gas) flow has different characteristics which may require custom solutions in sampling/monitoring same.

In the preferred embodiment of the present invention, two or more modular conditioning components are formed such that the diameter of the base of each component body includes a seal which slidingly engages the inner wall of a receiver such that, with the conditioning components stacked upon one another the components are enclosed so as to allow the flow of the sample serially therethrough, forming a conditioning and/or monitoring flow through passage through the assembly. The receiver is thereby formed to receive the stacked components, and engage the stacked components so as to retain the stack within the assembly in fixed fashion in use, but allow for easy disengagement and reconfiguration, maintenance, and/or repair when desired.

The present invention also contemplates a unique sealing mechanism so as to releaseably seal the stacked components to one another within the receiver, as well as a unique method of sampling utilizing an easily customizable modular sample component assembly configured for diverse applications, including use as a sample probe tip.

Finally, the present invention contemplates a unique modular sampling/conditioning/monitoring component, which is designed to receive one or more sub-components therein of diverse functionality, so as to provide easily customizable configurations, while maintaining general uniform characteristics for sealable, serial-flow in a stacked engagement.

DESCRIPTION OF THE FIGURES

FIG. 3A is a side view illustrating the stacked modular sampling components of FIG. 2, having a first threaded insert with flow passage forming the base of the stack, said first threaded insert formed to engage the ID of a receiver or cartridge, and a transition piece at the top of the stack to engage the inlet of a probe or the like.

FIG. 3B is a side view illustrating an exemplary receiver or cartridge formed to receive the stack of FIG. 3A.

FIG. 3C is a side, cut-away view of the stacked modular sampling components of FIG. 3A engaging the receiver of FIG. 3B.

FIG. 5A is a side view illustrating a probe tip adapter to allow the receiver with conditioning component stack (with sub-components situated therein) to be mounted as a sampling probe tip for analytical sampling of a process gas stream or the like.

FIG. 5B is a side view illustrating an alternative receiver or cartridge configuration of FIG. 5A to receive the stack of FIG. 3A shown mounted to a probe tip.

FIGS. 8A-8F illustrate the components and working relationship of the various elements of the probe carrying the probe tip of FIG. 7.

DETAILED DESCRIPTION OF THE PRESENT INVENTION

Figure 1:
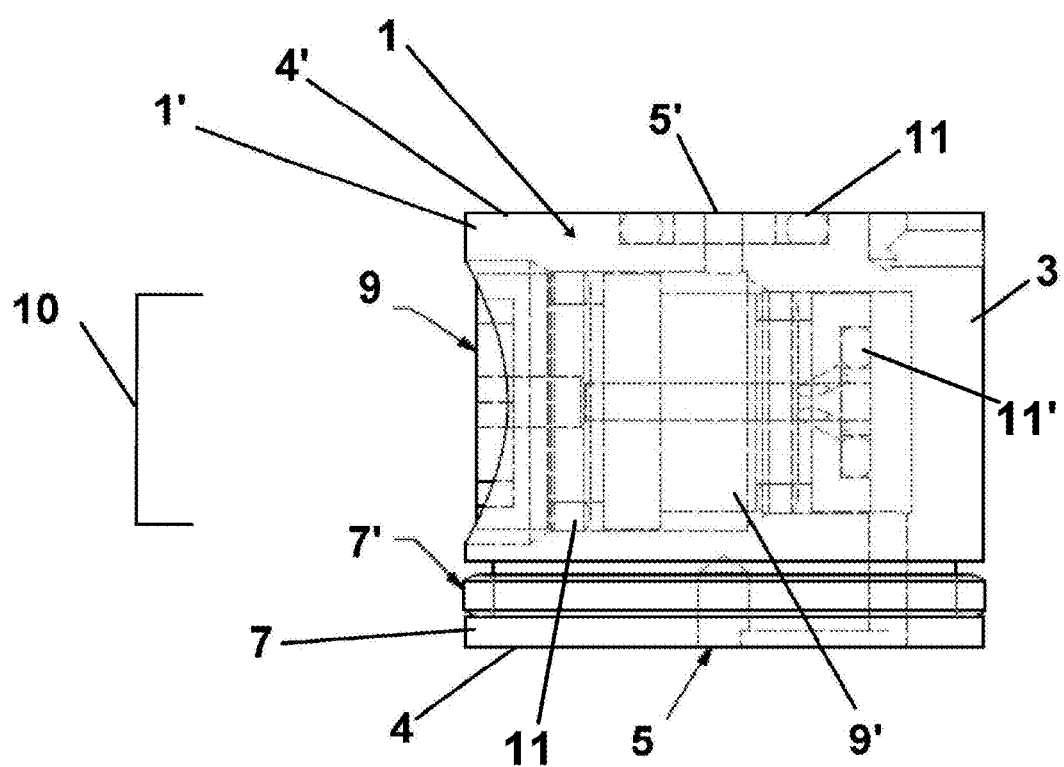
FIG. 1 is a side view of an exemplary stackable modular sample conditioning component of the preferred embodiment of the present invention, with exemplary inner workings shown in phantom, in this case, a side-mounted, flow-through pressure regulator.
Figure 2:
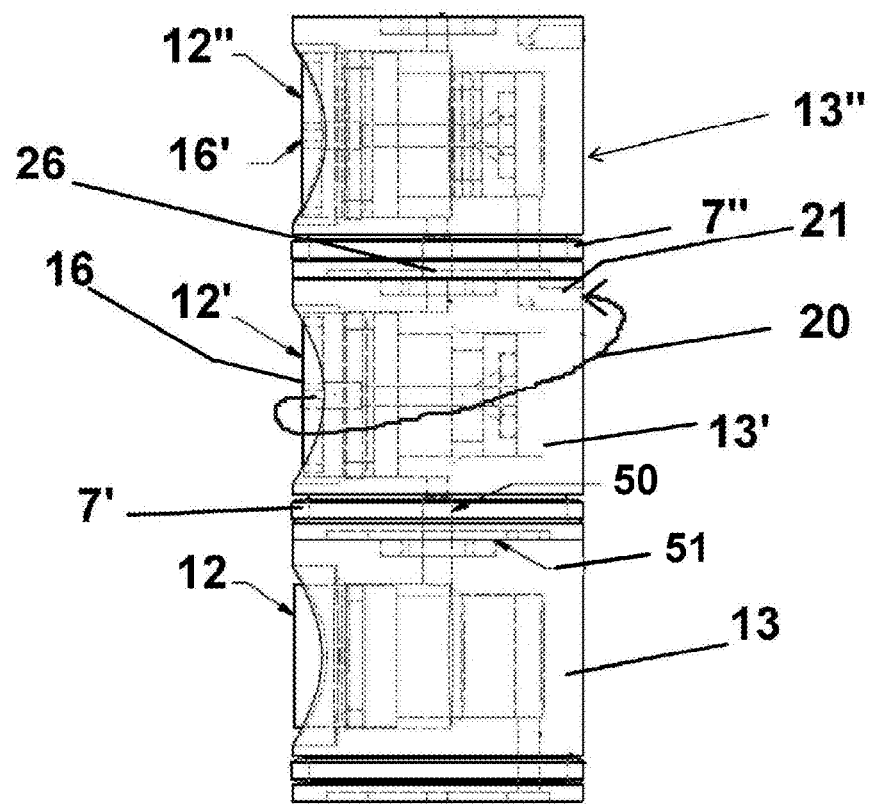
FIG. 2 is a side view of three stackable modular sample conditioning components in stacked configuration.
Figure 3D:
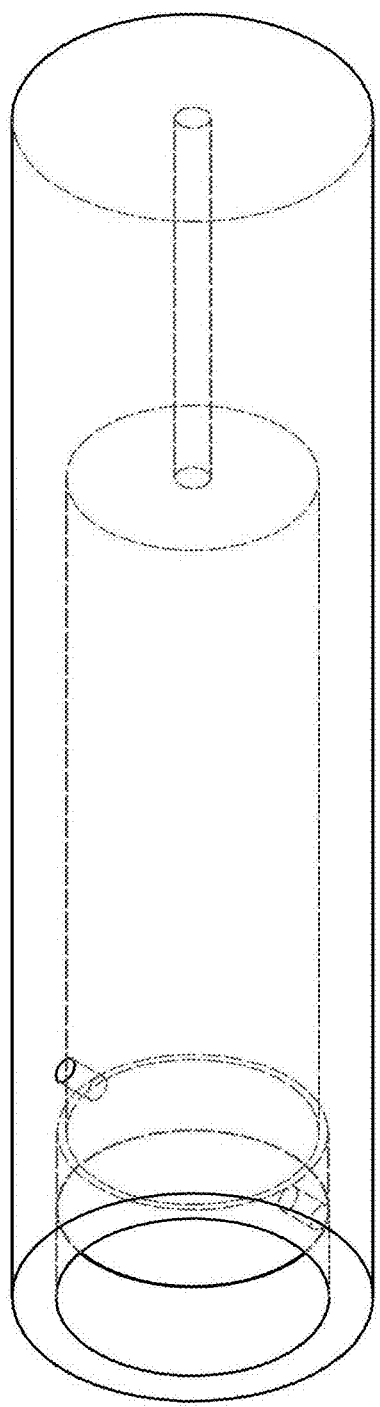
FIG. 3D is a side, perspective view of an alternative of the receiver or cartridge of FIG. 3B.
Figure 4B:
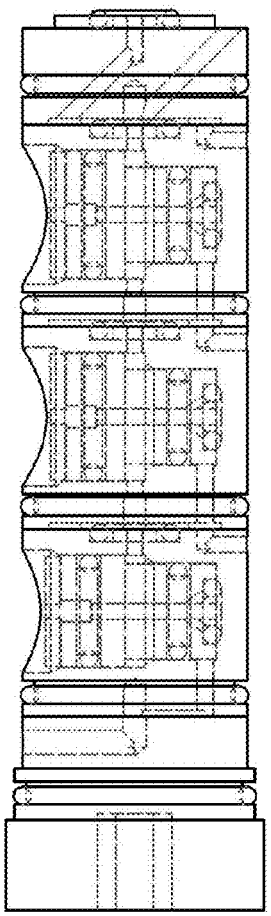
FIG. 4B is a side view of FIG. 4A, illustrating the sub-components and modular sampling components in phantom.
Figure 4A:
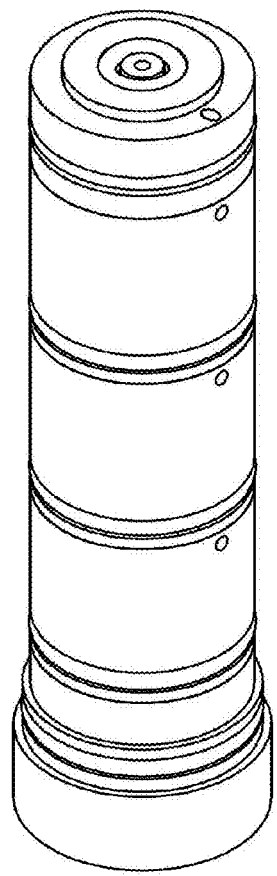
FIG. 4A is a perspective view of the stacked modular sampling components with base and transition piece of FIG. 3A.
Figure 4D:
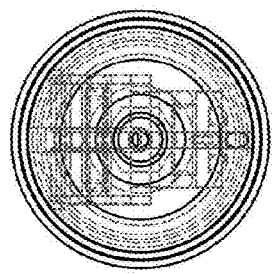
FIG. 4D is a top, end view of the apparatus of FIG. 4B.
Figure 4C:
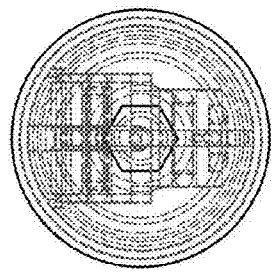
FIG. 4C is a bottom, end view of the apparatus of FIG. 4B.

Continuing with FIG. 1, the preferred embodiment of the present invention utilizes a unique modular component 1 which may have one or more sampling, fluid conditioning or monitoring functions or the like, each component comprising a component body 1' having an outer wall 3, and first 4 and second 4' ends having inlet 5 and outlet 5' flow passages, respectively. The component body also has a base 7 at the first end 4, the base having a seal 7' thereabout to engage the inner wall of the receiver (inner wall 22 of the receiver 23 is shown in FIGS. 4 and 5 and discussed in more detail infra.)

As shown, in the preferred embodiment of the present invention, the component body 1' has an opening 10 formed in the outer wall 3 of the unit forming a cavity 9' formed to receive a sub-component 9 (and which may include o-ring seals 11', 11"), which sub-component is configured to provide the desired functionality with regard to fluid conditioning, monitoring, etc, and is designed for inter-changeability engaging the passages formed in the modular component 1. It is noted that the opening 10 formed to receive the sub-component may be threaded or not, depending upon the type of sub-component used and its operation. For example, presently the opening 10 may not be threaded for use with the pressure regulator stage as shown because it must move to operate, although many other sub-components would threadingly engage opening 10, as currently envisioned.

The exemplary sub-component 9 shown in FIG. 1 comprises a pressure regulator stage or reducer (for example, a first stage regulator), which is inserted into the opening 10 and engages same (sealed via o-ring, for example), such that said regulator stage or the like is situated largely within the component body, and does not protrude past the largest diameter of the sidewall.

As shown, the sub-component 9 (as indicated, a regulator stage) is configured to engage the inlet 5 and outlet 5' flow passages in its operation.

A sealing mechanism in the form of an o-ring is shown at the end of the component, so as to provide a fluid-tight seal between adjacent, stacked components.

The preferred embodiment of the present invention employs multiple stacked components to provide flow through modular conditioning, monitoring, or the like. The stacked components could be secured to one another (via example, threaded or snapped connections, or external brackets or the like), and may be simply stacked in sliding engagement with a receiver (the example illustrated in the present FIGS. 1-6) or cartridge, or may be some combination thereof. The components are selected depending upon the fluid conditioning or monitoring required, then stacked in the desired order of conditioning/monitoring.

Continuing with FIGS. 1-6, first 13, second 13' and third 13" components are shown stacked upon one another (FIG. 2), the first 13 component having installed as its sub-component 12 an inlet filter, membrane filter, coalescing filter, particulate filter or the like, the second 13' component having at its sub-component 12' a stage one regulator, and the third 13" component having a sub-component 12" comprising a second stage regulator.

As shown, each component has at its second end 4' a sealing mechanism (11 in FIG. 1 or 51 in FIG. 2) such as an o-ring or the like situated about the outlet flow passage 5' to provide sealed fluid passage communication to the first end 4 of the stacked component or other item engaged thereto (which may serve as a reference port for a regulator, and each component has at its first end 4 a base 7 which has a seal 7' about its outer perimeter formed to engage the inner wall 22 of receiver 23.

Continuing with FIGS. 1-4, to accommodate sub-components such as the regulators or the like shown in the exemplary second 13' and third 13" stacked components having an outlet 16, 16' emanating therefrom, the outer wall 3 of the component body is formed to have a slightly lesser width 17' (or diameter in the case of a cylindrical configuration) than the inner wall 22 (or ID in the case of a cylinder) of the receiver 23 for sliding engagement and also so as to form a space 18 therebetween (in the present, preferred embodiment, the space being about 0.005"), said space 18 enclosed via opposing component base seals 7', 7" engaging the inner wall of the receiver, forming an enclosed passage allowing outflow 20 from the sub-component outlet 16 to inlet passage 21 leading to the next component, in the present example, a stage two regulator. In the illustrated, exemplary embodiment, outlet flow passage 26, 50 provides the reference pressure for the stage two regulator stacked thereupon.

Continuing with FIGS. 1-5, a threaded insert 27 is applied to the first end of the first component 13 to engage the threaded opening 27' of the receiver 23 or cartridge, to retain the stack of components solidly within the receiver or cartridge, and apply pressure to the stack of components to facilitate the o-ring sale between said components, while the flow passage formed therethrough (in FIG. 4, inlet 53, outlet 54) allows passage of the flow to or from the components. Also, a transition piece 28 may be provided to engage the second end of the last component forming the stack, the transition piece engaging the outlets of said last component and directing same via passages to form the desired outflow for the system, as well as being formed to engage the inlet of the receiver, cartridge, probe or other item having its inlet engaged thereto.

Figures 5A, 5B:
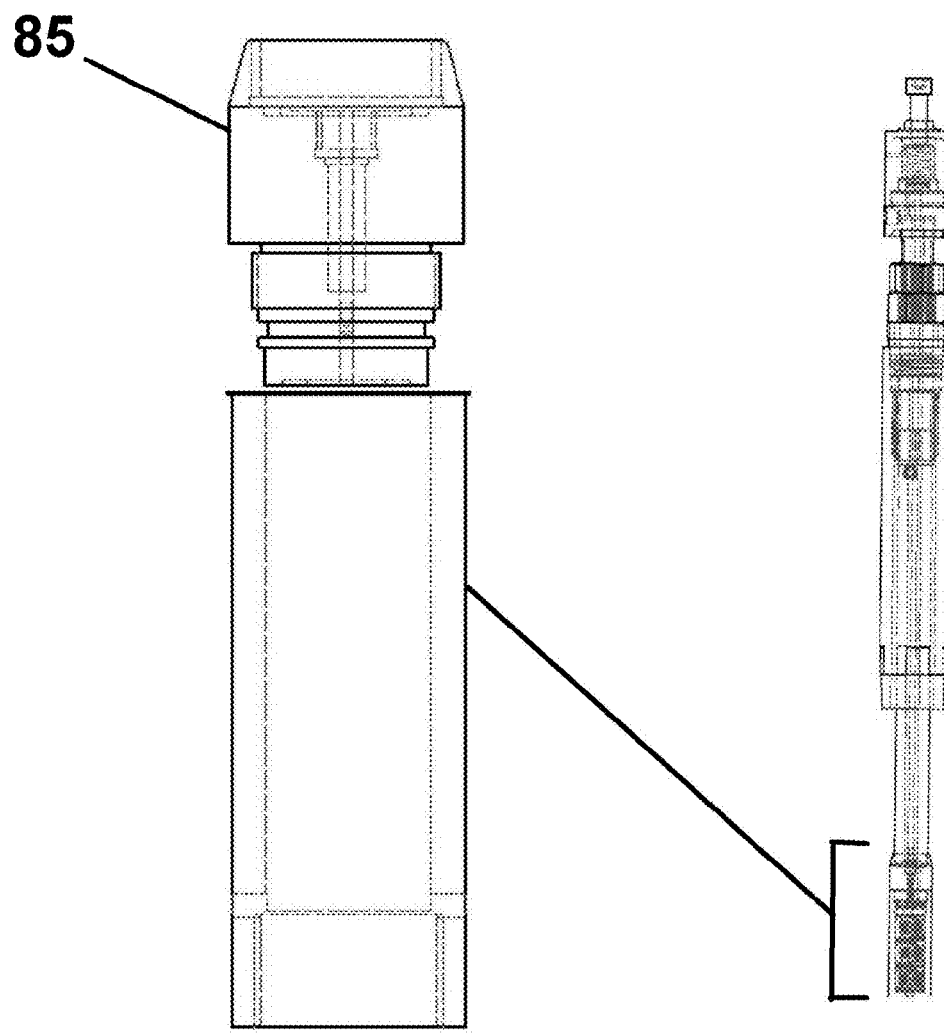
Figure 5C:
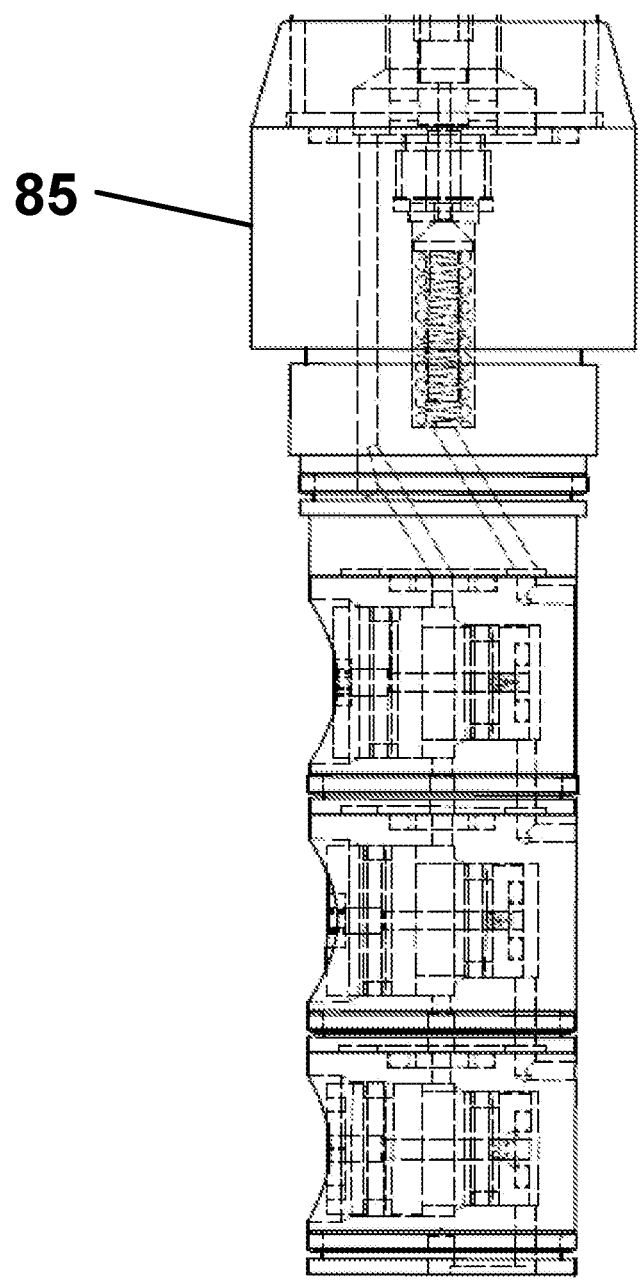
FIG. 5C is a partial, cut-away view of the device of FIG. 5B shown without the receiver/cartridge, engaging an exemplary modular sample component stack with sub-components situated therein.
Figure 6:
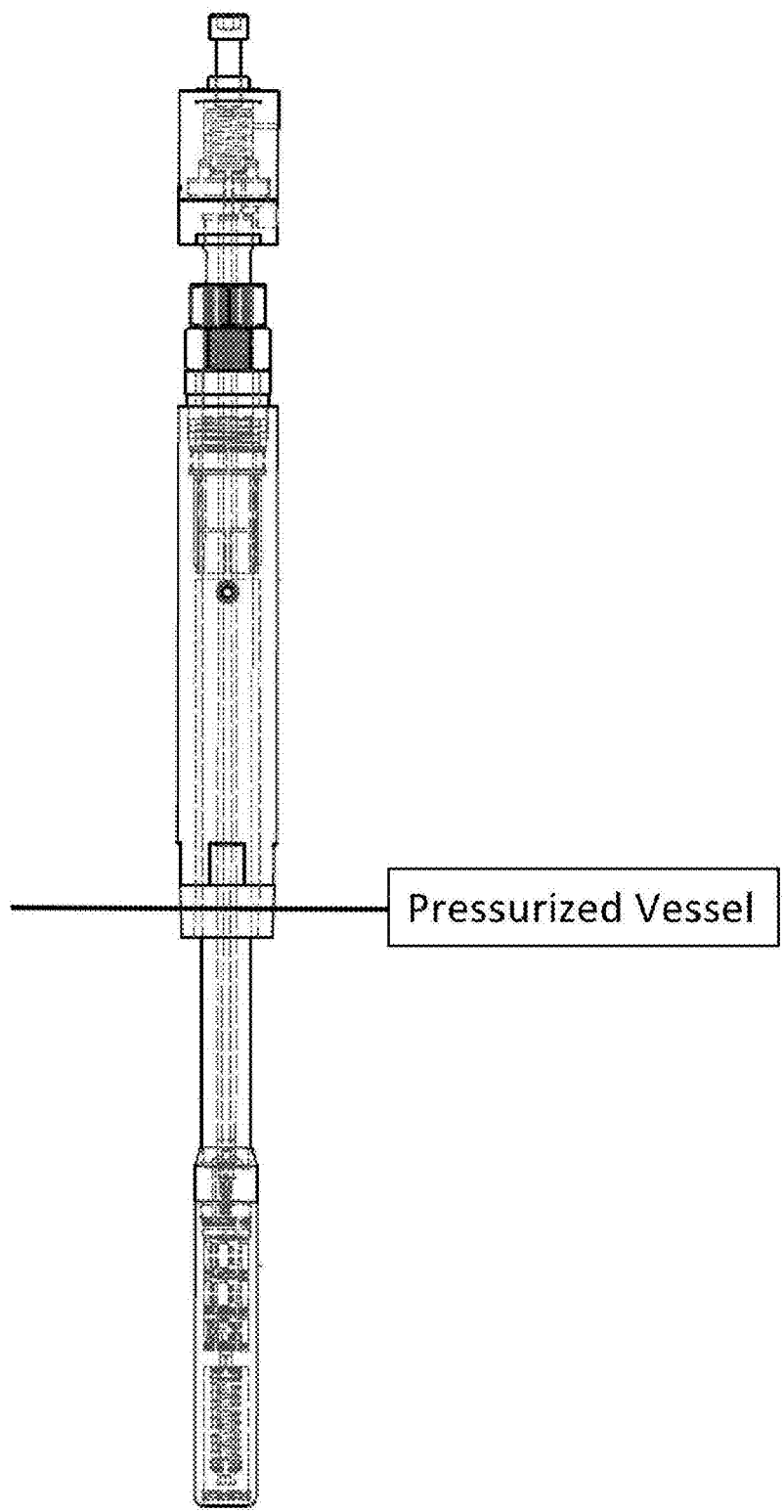
FIG. 6 is a side view of a probe tip cartridge/protective shroud having multiple sampling components in the form of staged pressure regulators for controlled reduction in fluid pressure (for example, to lessen or prevent JT cooling), the regulators situated in stacked fashion (in phantom) in a receiver, preceded by a phase separation membrane at the (extended) probe tip.
Figure 7:
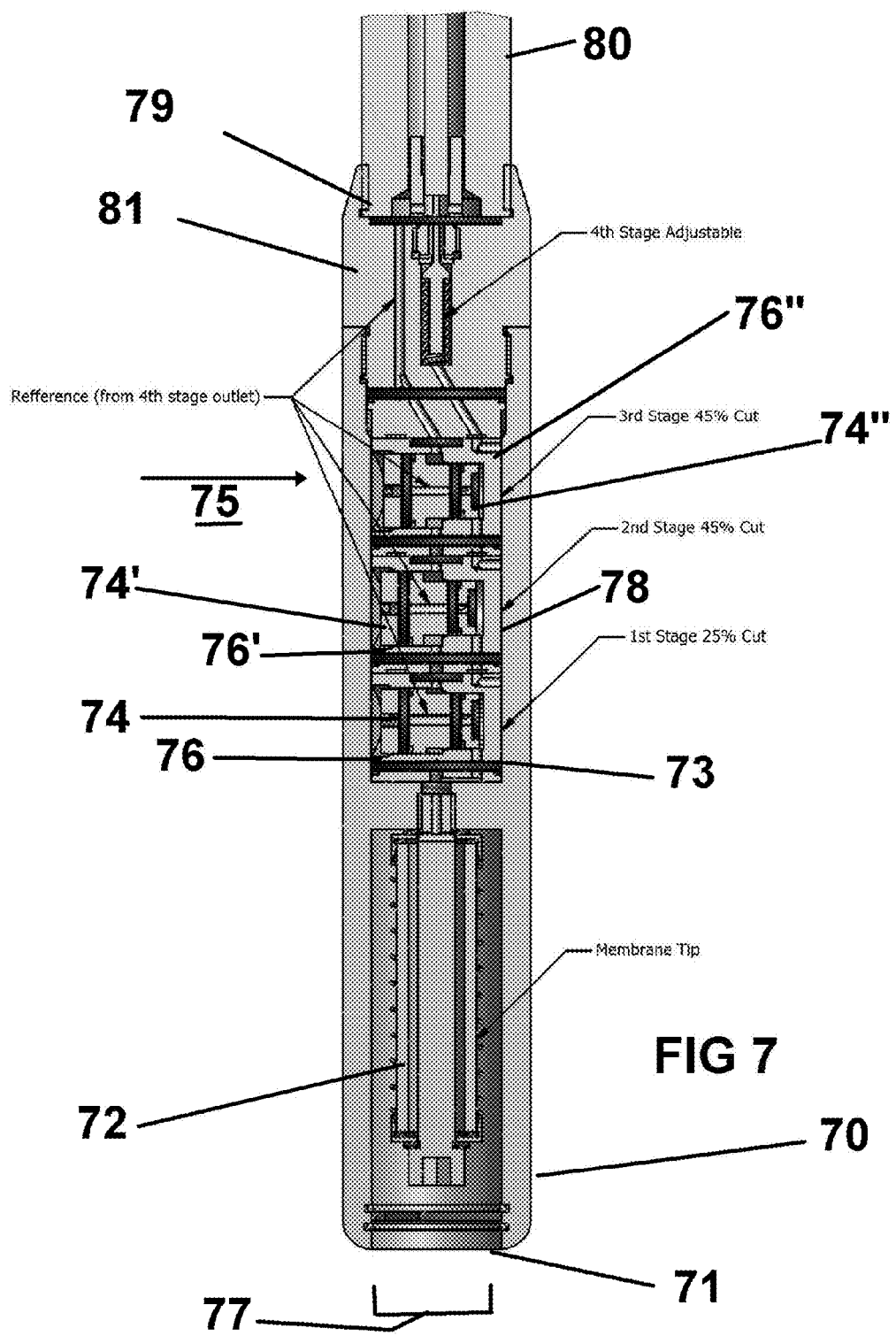
FIG. 7 is a side, cut-away view of the exemplary probe tip of FIG. 6 and the various components in stacked, serial, flow-through communication therethrough.
Figure 8D:
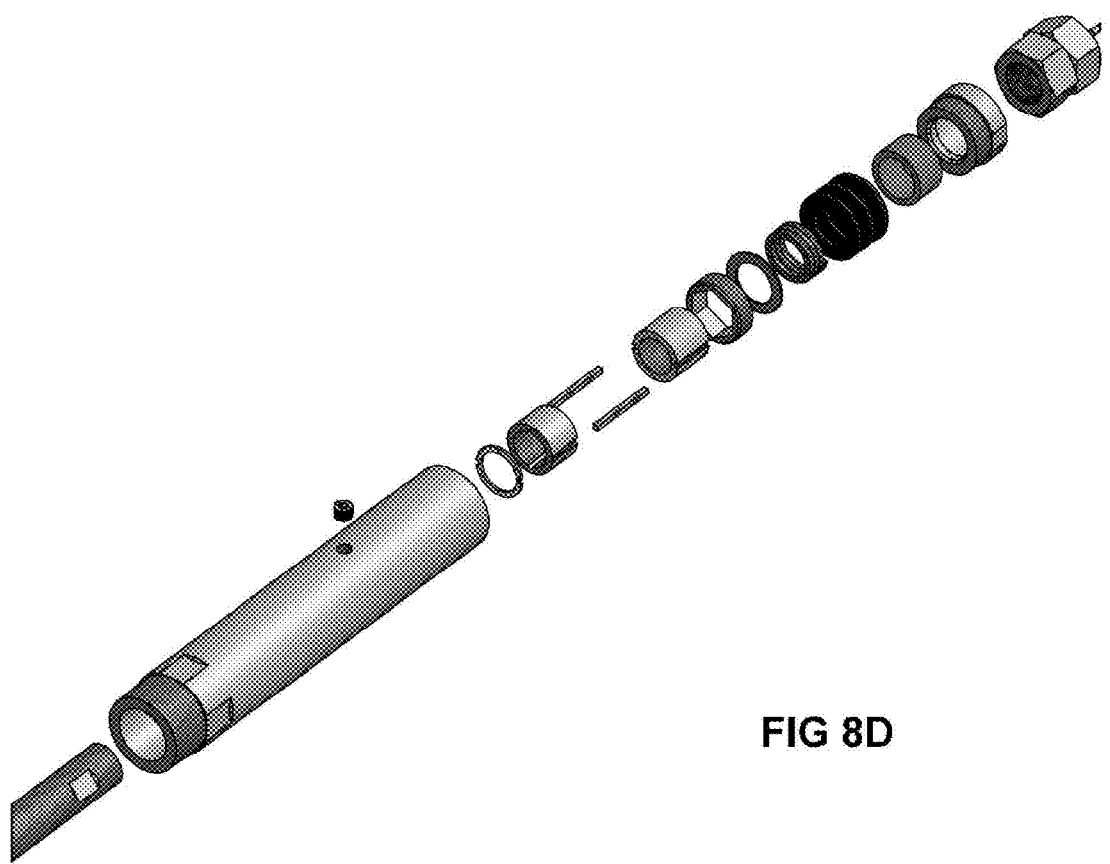
Figure 8E:
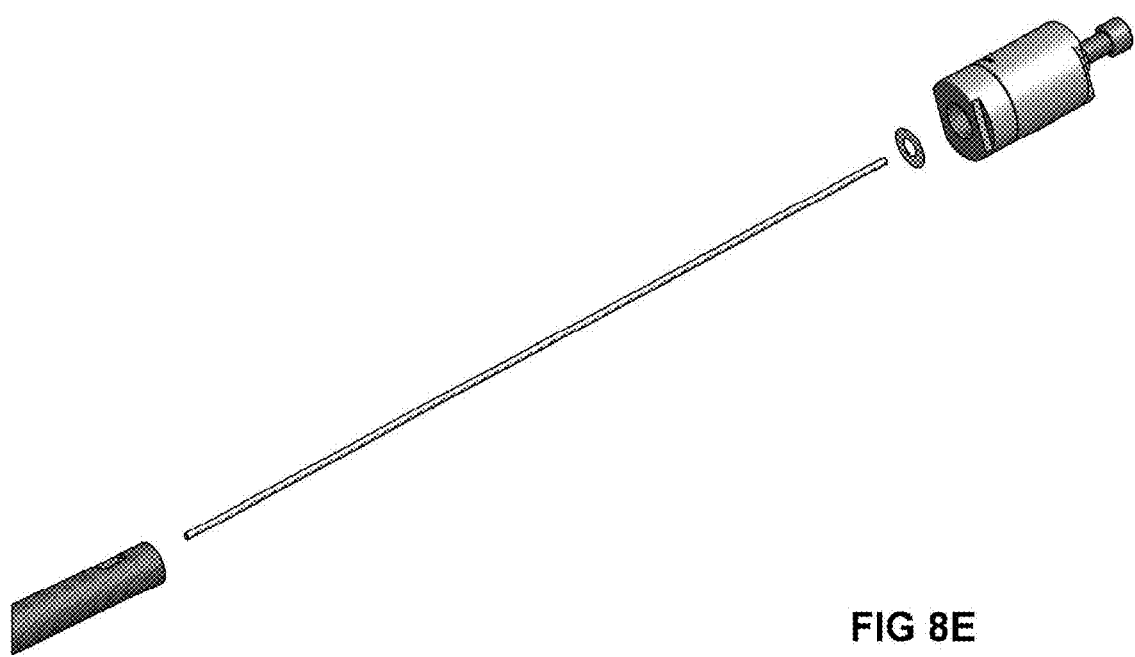
Figure 8F:
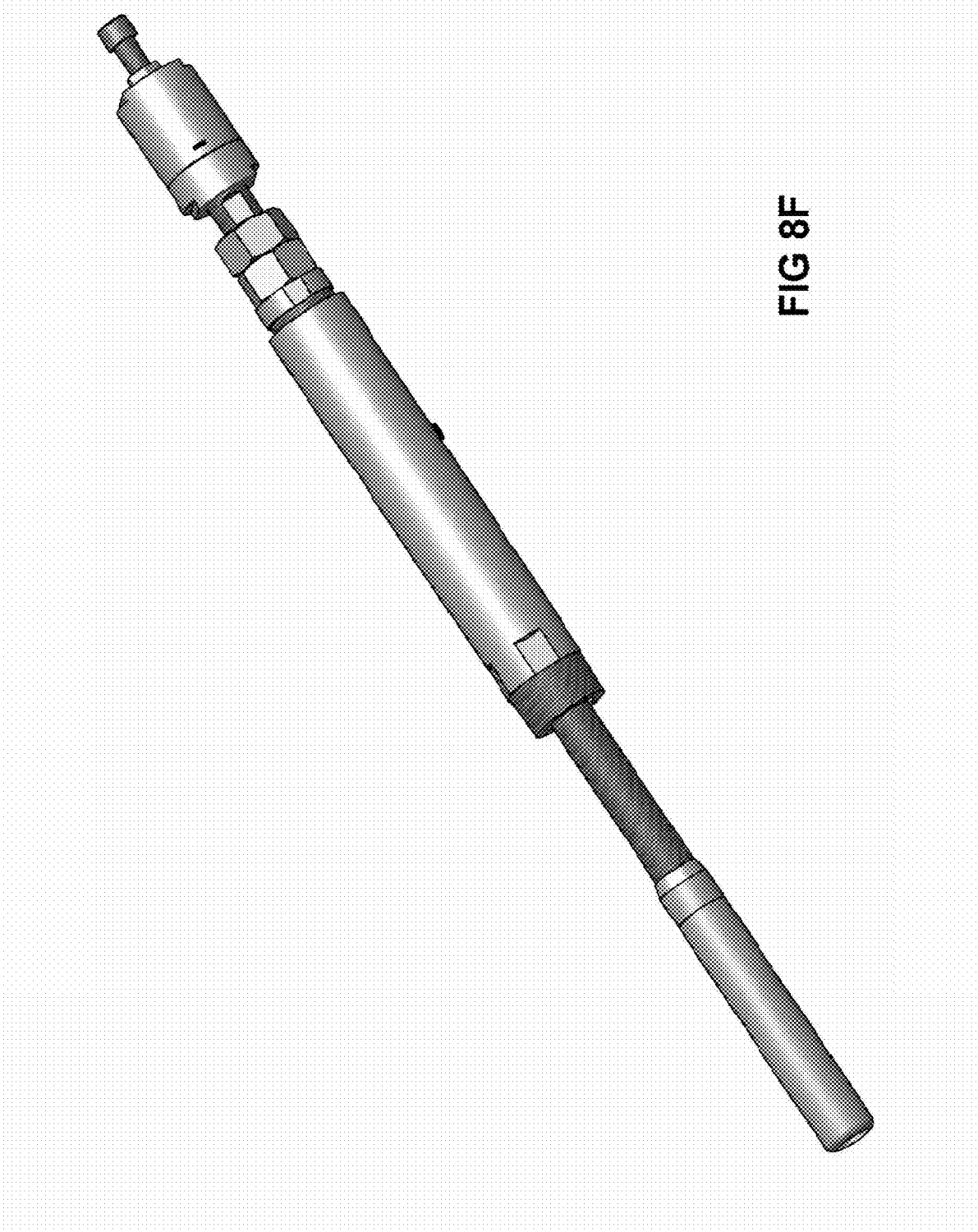

As shown in FIGS. 5A-C, the cartridge with modular sample components stacked therein may be mounted to the tip of a fluid probe or the like via a probe tip adapter to allow the stack to serially engage a process fluid stream. In such a scenario, fluid from the fluid stream would into the probe tip, through the first then subsequent conditioning components in serial fashion, and thereby provide a flow of conditioned fluid from the process fluid stream at prevailing fluid pressure and temperature to the probe, providing an analytically correct sample, while lessening any JT cooling effect.

Another example of stacked conditioning components, in this example contained in a cartridge configured to form a probe tip extension 70 mounted to a probe, can be found in FIGS. 6-8D. As shown, a probe tip as situated at its opening 71 a phase separation membrane 72, coalescing filter, particulate filter, or the like, followed by a receiver 73 formed in the cartridge to contain first 74, second 74' and third 74" stage, stacked pressure regulator sub-components side-mounted 75 in three respective conditioning components 76, 76', 76" of a uniform outer diameter (OD) 77 slidingly engaging the inner diameter (ID) 78 of receiver 73. While pressure regulators as conditioning sub-components are illustrated as used, conditioning sub-components of other functions may be selected depending upon the fluid conditioning desired, then stacked in the desired order of conditioning.

The cartridge with modular sample components therein is shown mounted to a tip 79 of a probe 80 or the like (and may include a 4th stage adjustable regulator 81 with opposing threaded ends for engagement therebetween) to selectively engage a process gas stream in a pressurized vessel such as a pipeline, so that the fluid passes into the probe tip, through the phase separation membrane 72 then the first and subsequent conditioning components, and thereby provide a flow of conditioned fluid from the process gas stream at prevailing pressure and temperature to the probe, in a manner which could lessen or prevent JT cooling.

In summary, the present invention contemplates the unique and useful improvement of providing modular conditioning components, each having their own function and specification, but designed to be interchangeably stacked depending upon the conditions and desired outcome which may be used as a connected stack and/or placed into a receiver or cartridge, thereby providing a custom conditioning and/or monitoring solution.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

We claim:

1. A modular conditioning apparatus for use with a pressurized fluid stream, comprising:
   a first modular component comprising an outer wall, first and second ends, an inlet flow passage, and an outlet flow passage;
   a housing having a receiver having an inner wall formed therein to receive and envelope said outer wall of said first modular component, said housing having first and second ends, said first end of said housing formed to engage a probe and provide outlet flow therefrom; and a seal associated with said first modular component formed to prevent leakage between said outer wall of said first modular component and said inner wall of said receiver;

wherein said first modular component is formed to be placed into said receiver of said housing so that said receiver envelopes same, said housing with modular component then inserted into the pressurized fluid stream via said probe so as to receive flow from said pressurized fluid stream via a flow path formed in said housing, said housing and first modular component therein formed to interact with said pressurized fluid stream at the prevailing pressure and temperature of said pressurized fluid stream to provide interacted gas from said first modular component.

2. The apparatus of claim 1, wherein there is provided a second modular component having inlet and outlet flow passages first and second ends, an outer wall, and a seal associated with said second modular component formed to prevent leakage of fluid around said second modular component, said second modular component formed to be received by said receiver of said housing, said inlet flow passage of said second modular component formed to engage said outlet flow passage of said first modular component to provide serial flow therethrough, wherein said first and second modular components engage one another end on end, and said receiver is formed to envelope said outer walls of said first and second modular components, and said seals of said first and second modular components form fluid barriers therebetween, respectively, so that said interacted gas from said first modular component serially flows to said second modular component.

3. The apparatus of claim 2, wherein said outer walls of said first and second modular components slidingly engage said receiver, respectively.

4. The apparatus of claim 2, wherein one of said first and second modular components threadingly engage said receiver.

5. The apparatus of claim 2, wherein said second modular component is stacked upon said first modular component, within said receiver.

6. The apparatus of claim 5, wherein said housing is mounted to the end of a probe, such that said housing forms a probe tip situated in said pressurized fluid stream, and wherein said housing is formed to provide flow of said interacted gas to said probe.

7. The apparatus of claim 6, wherein said housing is formed to receive fluid from said pressurized fluid stream.

8. The apparatus of claim 4, wherein said seal of said first and second modular components comprises first and second O-rings engaging said outer wall of said first and second and second modular components, respectively, said first and second O-rings also engaging said inner wall of said receiver, so as to prevent the migration of fluid therebetween.

9. The apparatus of claim 8, wherein at least one of said first and second modular components comprise a conditioning component to condition said fluid, such that said interacted fluid comprises conditioned fluid.

10. The apparatus of claim 9, wherein said conditioning component comprises at least one of a regulator, isokinetic sampling component, phase separation membrane, coalescing filter, particulate filter, inertial separators, or valve.

11. The apparatus of claim 8, wherein at least one of said first and second modular components comprise a monitoring component formed to monitor said fluid.

12. The apparatus of claim 11, wherein said monitoring component comprises at least one of a corrosion coupon, temperature sensor, pressure sensor, moisture sensor, or gas sensor.

13. The apparatus of claim 12, wherein said monitoring component is wireless.

14. The apparatus of claim 3, wherein said seal of said first and second modular components comprises first and second O-rings engaging said outer wall of said first and second and second modular components, respectively, and said inner wall of said receiver, so as to prevent the migration of fluid therebetween.

15. The apparatus of claim 14, wherein at least one of said first and second modular components comprise a conditioning component to condition said fluid, such that said interacted fluid comprises conditioned fluid.

16. The apparatus of claim 15, wherein said conditioning component comprises at least one of a regulator, isokinetic sampling component, phase separation membrane, coalescing filter, particulate filter, inertial separators, or valve.

17. The apparatus of claim 14, wherein at least one of said first and second modular components comprise a monitoring component formed to monitor said fluid.

18. The apparatus of claim 17, wherein said monitoring component comprises at least one of a corrosion coupon, temperature sensor, pressure sensor, moisture sensor, or gas sensor.

19. The Apparatus of claim 18, wherein said monitoring component is wireless.

20. The apparatus of claim 3, wherein said seal is provided at an end of said first and second modular components such that said seal engages said components upon end to end engagement of same to facilitate the contained flow of fluid therebetween.

21. The apparatus of claim 20, wherein said seal at said end of said first and second modular components comprises an O-ring.

22. The apparatus of claim 1, wherein said seal is situated between said outer wall of said first modular component and said inner wall of said receiver.

23. The apparatus of claim 22, wherein said seal comprises an O-ring engaging said outer wall of said first modular component and said inner wall of said receiver.

24. A sampling apparatus, comprising:

First and second modular components, each having unique fluid interactive features, said components formed to be slidingly received in a receiver having an inner wall forming a clearance therebetween, said components being stacked one upon the other for sealed engagement, so as to form a serial flow-through passage to engage fluid as it flows therethrough;

Said first and second modular components having a seal formed to prevent leakage of fluid in said clearance formed between said modular components and said inner wall of said receiver;

Said receiver formed in a housing, said housing formed for insertion into a pressurized fluid stream so that said first modular component therein receives flow from said pressurized fluid stream at the prevailing pressure and temperature of said pressurized fluid stream.

25. The apparatus of claim 24, wherein at least one of said first and second modular components comprise fluid conditioning components formed to selectively condition fluid as it flows therethrough.

26. The apparatus of claim 24, wherein said first and second modular components comprise fluid conditioning components formed to selectively condition fluid as it flows therethrough.

27. The apparatus of claim 26, wherein there is provided an additional modular component.

28. The apparatus of claim 27, wherein at least one of said conditioning components are selected from a group comprising at least one of a regulator, isokinetic sampling component, phase separation membrane, coalescing filter, particulate filter, inertial separators, or valve.

29. The apparatus of claim 24, wherein at least one of said first and second modular components comprise fluid monitoring components formed to selectively monitor fluid as it flows therethrough.

30. The apparatus of claim 24, wherein said first and second modular components comprise fluid monitoring components formed to selectively monitor fluid as it flows therethrough.

31. The apparatus of claim 30, wherein there is provided an additional modular component.

32. The apparatus of claim 31, wherein at least one of said monitoring components are selected from a group comprising at least one of a corrosion coupon, pressure sensor, moisture sensor, liquid detector, gas sensor, temperature sensor, wireless monitoring devices, sample container, or flow meter.

33. The apparatus of claim 24, where said stacked components have a diameter and a base, and wherein said diameter of said base has mounted thereto a seal formed to slidingly engage the inner wall of the receiver such that, when the components are stacked upon one another, the components, seal and inner wall of said receiver form an enclosure, ensuring the contained flow of fluid serially through each of said stacked components.

34. The method of sampling a fluid, comprising the steps of:
   a) establishing a fluid communication order of sample components to effect selective interaction of the fluid;
   b) providing sample components, each having a desired fluid interaction feature, to provide the selective interaction in step "a";
   c) stacking said sample components so as to provide fluid communication from one of said sample components to another in serial communication, providing stacked components;
   d) enclosing said stacked components in a receiver, using said receiver to envelope said stacked components, while sealingly engaging said stacked components to one another to facilitate the serial flow of fluid therebetween;
   e) mounting said receiver with stacked components to an insertion probe so as to form a probe tip having an opening;
   f) inserting said probe tip into a pressurized fluid flow;
   g) facilitating the flow of fluid from said pressurized fluid flow into said probe tip opening;
   h) facilitating the flow of fluid serially through each of said sample components, each said sample component providing selective interaction with the fluid.

35. The method of claim 34, wherein in step "b" at least one of said sample components comprise sample conditioning components selected from a group having selective conditioning features for fluid flowing therethrough; and in step "h" there is included the step of facilitating the flow of said fluid through said sample conditioning components to serially provide stepped fluid sample conditioning, providing a conditioned fluid.

36. The method of claim 35, wherein there is provided after step "h" the added step "i" of facilitating the flow of said conditioned fluid from said probe for collection.

37. The method of claim 34, wherein in step "b" there is provided the step of selecting at least one of said conditioning components from a group comprising at least one of a regulator, isokinetic sampling component, phase separation membrane, coalescing filter, particulate filter, inertial separators, or valve.

38. The method of claim 37, wherein in step "b" at least one of said sample components comprise sample monitoring components selected from a group having selective monitoring features to monitor fluid flowing therethrough; and in step "h" there is included the step of facilitating the flow of said fluid through said sample monitoring components to serially provide stepped fluid sample monitoring, providing a monitored fluid.

39. The method of claim 38, wherein there is provided after step "h" the added step "i" of facilitating the flow of said monitored fluid from said probe for collection.

40. The method of claim 39, wherein in step "b" there is provided the step of selecting at least one of said monitoring components from a group comprising at least one of a corrosion coupon, pressure sensor, moisture sensor, liquid detector, gas sensor, temperature sensor, wireless monitoring devices, or flow meter.

41. A method of conditioning a fluid, comprising the steps of:
   a) analyzing a sample of fluid from a fluid stream;
   b) establishing a desired sample fluid conditioning and/or monitoring protocol for fluid sampled from said fluid stream;
   c) providing modular components having sample fluid conditioning and/or monitoring capability as established in step "b";
   d) stacking said modular components one upon the other while engaging same so as to provide serial flow therethrough in the order determined in step "b", providing a modular component stack;
   e) engaging said modular component stack to a probe;
   f) facilitating the flow of fluid into one end of said modular component stack, through said component stack, while utilizing each said modular component to condition and/or monitor said fluid in serial fashion by each said modular component as said fluid passes therethrough.

42. The method of claim 41, wherein step "e" comprises the steps of e1 providing a housing having formed therein a receiver, e2 slidingly positioning said modular component stack within said receiver and engaging same thereto; and e3 mounting an end of said housing to said probe to form a probe tip.

43. The method of claim 42, wherein in said step "c" there is provided the added steps c1 of inserting into each modular component a sub-component chosen to facilitate the sample fluid conditioning and/or monitoring of step "b".

44. A method of sampling a fluid from a fluid stream, comprising the steps of:
   a) providing modular sample components formed to stack upon one another in serial flow fashion;
   b) providing modular sub-components, each said sub-component formed to engage via insertion to a modular sample component to provide fluid functionality thereto;

c) analyzing a sample of fluid from a fluid stream;
d) establishing a desired sample fluid conditioning and/or monitoring protocol for fluid sampled from said fluid stream;
e) selecting modular sub-components from those in step "b", providing chosen sub-components, and inserting each said chosen sub-components into a respective modular component to perform the functionality established in step "b";
f) stacking said modular components with sub-components one upon the other to provide serial flow therethrough in an order to achieve the protocol of step "d", providing a modular component stack;
g) engaging said modular component stack to an insertion apparatus;
h) inserting said insertion apparatus into a fluid stream;
i) allowing fluid to flow into one end of said modular component stack, through said component stack, while allowing said fluid to be conditioned and/or monitored in serial fashion by each said sub-component.

45. The method of claim 42, wherein one or more of said sub-components comprise stepped pressure regulators, and wherein step "i" further comprises the step of allowing said fluid to serially pass through said regulators to provide stepped pressure reduction.

46. The method of claim 44, wherein in step "b" at least one of said sub-components are for sample conditioning of fluid flowing therethrough; and in step "i" there is included the step of allowing said fluid to flow through said sub-component to serially provide stepped fluid sample conditioning, providing a conditioned fluid.

47. The method of claim 46, wherein there is provided after step "i" the added step "j" of allowing said conditioned fluid to flow from said insertion apparatus for collection.

48. The method of claim 47, wherein in step "b" there is provided the step of selecting at least one of said conditioning sub-components from a group comprising at least one of a regulator, isokinetic sampling component, phase separation membrane, coalescing filter, particulate filter, inertial separators, or valve.

49. The method of claim 44, wherein in step "b" at least one of said sub-components comprise sample monitoring components selected from a group having selective monitoring features on fluid flowing therethrough; and in step "i" there is included the step of allowing said fluid to flow through said sample sub-component(s) to serially provide stepped fluid sample monitoring, providing a monitored fluid.

50. The method of claim 49, wherein there is provided after step "i" the added step "j" of allowing said monitored fluid to flow from said insertion apparatus for collection.

51. The method of claim 50, wherein in step "b" there is provided the step of selecting at least one of said monitoring sub-components from a group comprising at least one of a corrosion coupon, pressure sensor, moisture sensor, liquid detector, gas sensor, temperature sensor, wireless monitoring device, or flow meter.

52. The method of claim 44, wherein in step "a" said modular sample components have a side wall there is further provided the step "ai" of providing in said sidewall of said modular sample components a sub-component receiver formed for receiving modular sub-components.

53. The method of claim 52, wherein in step "e" said sub-components are inserted into the sub-component receiver provided in said respective modular component.

* * * * *